US009422622B2

(12) United States Patent
Storey

(10) Patent No.: US 9,422,622 B2
(45) Date of Patent: Aug. 23, 2016

(54) FLEXIBLE CONDUCTIVE SINGLE WIRE

(71) Applicant: Daniel M. Storey, Longmont, CO (US)

(72) Inventor: Daniel M. Storey, Longmont, CO (US)

(73) Assignee: SURFATEK LLC, Longmont, CO (US)

(*) Notice: Subject to any disclaimer, the term of this patent is extended or adjusted under 35 U.S.C. 154(b) by 912 days.

(21) Appl. No.: 13/644,091

(22) Filed: Oct. 3, 2012

(65) Prior Publication Data

US 2013/0046368 A1  Feb. 21, 2013

Related U.S. Application Data

(63) Continuation-in-part of application No. 12/586,031, filed on Sep. 16, 2009, now abandoned, which is a continuation-in-part of application No. 11/542,557, filed on Oct. 3, 2006, now abandoned.

(60) Provisional application No. 60/763,262, filed on Jan. 30, 2006.

(51) Int. Cl.
*C23C 14/20* (2006.01)
*C23C 14/32* (2006.01)
*A61N 1/05* (2006.01)
*A61N 1/375* (2006.01)
*H01J 37/32* (2006.01)

(52) U.S. Cl.
CPC ............. *C23C 14/325* (2013.01); *A61N 1/05* (2013.01); *A61N 1/3752* (2013.01); *C23C 14/20* (2013.01); *H01J 37/32412* (2013.01)

(58) Field of Classification Search
None
See application file for complete search history.

(56) References Cited

U.S. PATENT DOCUMENTS

| 4,280,514 | A | 7/1981 | MacGregor |
|---|---|---|---|
| 4,407,561 | A | 10/1983 | Wysocki |
| 4,418,984 | A | 12/1983 | Wysocki et al. |
| 4,549,548 | A | 10/1985 | Wittkampf et al. |
| 4,975,230 | A | 12/1990 | Pinkhasov |
| 5,342,283 | A | 8/1994 | Good |
| 5,454,886 | A | 10/1995 | Burrell et al. |
| 5,609,629 | A | 3/1997 | Fearnot et al. |
| 5,910,170 | A | 6/1999 | Reimink et al. |
| 5,984,963 | A | 11/1999 | Ryan et al. |
| 6,174,329 | B1 | 1/2001 | Callol et al. |
| 6,282,349 | B1 | 8/2001 | Griffin |
| 6,792,316 | B2 | 9/2004 | Sass |
| 6,846,556 | B2 | 1/2005 | Boire et al. |
| 7,077,837 | B2 | 7/2006 | Sahagian |
| 2002/0022781 | A1 | 2/2002 | McIntire et al. |
| 2003/0143335 | A1 | 7/2003 | Qiu et al. |
| 2003/0153981 | A1 | 8/2003 | Wang et al. |
| 2003/0165633 | A1 | 9/2003 | Ryu et al. |
| 2004/0054399 | A1 | 3/2004 | Roth |
| 2005/0187466 | A1 | 8/2005 | Glocker et al. |
| 2007/0178222 | A1* | 8/2007 | Storey et al. ............... 427/2.24 |
| 2010/0057179 | A1* | 3/2010 | Storey ............................ 607/119 |

FOREIGN PATENT DOCUMENTS

| DE | 42 11 956 | 5/1993 |
|---|---|---|
| EP | 0564819 | 10/1993 |
| WO | WO 03/044240 A1 | 5/2003 |

OTHER PUBLICATIONS

Utsumi, T. et al. "Study of electrode products emitted by vacuum arcs in form of molten metal particles" *Journal of Applied Physics*, Jan. 1975, pp. 126-131, vol. 46, No. 1.
Vyskocil, J. et al. "Cathodic arc evaporation in thin film technology" *Journal of Vacuum Science and Technology: Part A*, Jul./Aug. 1992, pp. 1740-1748, vol. 10, No. 4.
"Visual Acuity of the Human Eye" accessed Nov. 16, 2011, NDT Resource Center, http://www.ndt-ed.org/EducationResources/CommunityCollege/PenetrantTest/introduction/visualacuity.htm, pp. 1-3.
"Water" accessed Nov. 16, 2011, Georgia State University, http://hyperphysics.phy-astr-gsu.edu/hbase/chemical/water.html, pp. 1-2.
"What is a stent?" Obtained Jul. 5, 2012, U.S. Department of Health and Human Services http://www.nhibi.nih.gov/health/health-topics/topics/stents/, p. 1.

* cited by examiner

*Primary Examiner* — Sheeba Ahmed

(74) *Attorney, Agent, or Firm* — Saliwanchik, Lloyd & Eisenschenk

(57) ABSTRACT

Thin conductive metal coatings suitable for flexible non-metal fine wires and leads are described. Polymer clad silica fiber cores are produced by plasma coating with single or dual layers of metals such as silver, gold or titanium to provide micro thin leads such as those used for pacemakers and fracture resistant aircraft wires that are both conductive and resistant to flexing breakage. The metal surfaces can be used to transmit analog signals while the nonmetal cores can be designed to transmit digital signals. Select deposition conditions can produce nanorough metal coating surfaces which promote cell adhesion so that tissue scarring in vivo is greatly reduced.

17 Claims, 6 Drawing Sheets

FLEXIBLE CONDUCTIVE SINGLE WIRE

CROSS-REFERENCE TO RELATED APPLICATIONS

This application is a continuation-in-part of U.S. application Ser. No. 12/586,031, filed Sep. 16, 2009, which is a continuation-in-part of U.S. application Ser. No. 11/542,557, filed Oct. 3, 2006, which claims the benefit of U.S Provisional Application Ser. No. 60/763,262, filed Jan. 30, 2006, each of which is incorporated herein by reference in its entirety.

BACKGROUND OF THE INVENTION

1. Field of the Invention

The invention relates to microthin conductive, radiopaque metal coatings on nonmetal substrates and in particular to thin, flexible fine wire leads used in vivo for implanted monitoring devices and for signal or communication wires subject to bend and flex stress.

2. Description of Background Art

Cardiac pacing is a proven means of maintaining heart function for patients with various heart conditions. Over 650,000 pacemakers are implanted annually in patients worldwide, including over 280,000 in the United States. Over 3.5 million people in the developed world have implanted pacemakers. Another approximately 900,000 have an implantable cardioverter defibrillator (ICD) or cardiac resynchronization (CRT) device. Pacemakers use an average of about 1.4 implanted conductive leads during their service life and ICD and CRT devices use an average of about 2.4 leads.

Lead failure is a serious and in some situations life threatening problem for pacemakers and ICD and CRT devices. The average number of leads used per unit indicates the high incidence of lead failure, which is due to two main failure modes for current leads.

Failure of a lead body may occur due to cracking or breaking of the conductor in the lead. This often arises due to repeated flexing from the beating of the heart and associated muscular movements that stress the pathway from the pacemaker to the heart. This subjects the lead at a series of points along its length to tens of millions of cycles per year over a lead's lifetime. Currently available wire leads have not been durable enough to withstand this rigorous environment and many have experienced failure due to conductor fatigue.

Recently, the U.S. Food and Drug Administration has asked a medical manufacturer of heart devices to initiate studies to determine the unusual frequency of breakage in wire leads connecting the heart to certain brands of defibrillators. Such failures are potentially life threatening because implantable devices such as defibrillators may be crucial in restoring irregular and abnormal heart rhythms. Breakages of wires inside leads in some of the devices have occurred in as high as 19% of 700 devices in recent use. In an effort to detect potential breakages, the FDA is recommending X-ray studies post implant to detect any potential wire insulation problems, which would indicate future wire breakage.

A second cause of lead failure is dislodgment or fouling of the distal end, thereby rendering the lead inoperable. The distal end can become non-functional in two distinct ways. Dislodgment of the end from the muscle may occur. While not common, the heart muscle in constant motion can unseat the tine, causing lost contact with the area that needs the voltage for correct pacing. A more common occurrence is the buildup of scar tissue around the insertion point due to the body's natural foreign body response and the healing response initiated from insertion of the electrode into the heart. Buildup of scar tissue may also occur from abandoned leads that have not been removed. Increased resistance of an active connection causes a larger draw of power from the generator in order to correctly pace the heart. Both failure modes can be fatal.

The generator/control unit that controls pacing is implanted under but near the skin surface. Leads are routed from the generator to the heart probes to provide power for pacing and data from the probes to the generator. Probes are generally routed into the heart through the right, low pressure side of the heart. For access to the left side, lead wires are generally from the right side through the coronary sinus and into veins draining the left side of the heart. This access path has several drawbacks; the placement of the probes is limited to areas covered by veins; leads occlude a significant fraction of the vein cross section; and, the number of probes is limited to one or two.

Ideally a lead should be evenly coated with a conducting surface so that current flows into a device to which it is connected. Unfortunately metal coatings on nonmetal surfaces such as plastics tend to lack adherence, and often do not cover the entire surface because many coating processes are satisfactory only on flat surfaces. Fixturing, the process for coating complex surfaces, is a challenge with round shapes or surfaces that are not electrically conductive. In many applications, bands, stripes or other radiopaque markers are preferable to whole surface coverage.

Application of a seed layer to non-conductive materials is generally a significant problem. This usually requires complex masking along with the use of a different deposition technique such as sputtering or ion beam assisted deposition (IBAD). This is a costly step leading to handling problems, increased cost due to the double processing and often results in poor coating adhesion.

Plastic parts are not easily metal coated because plastic is a nonconductor of electricity. One approach to this problem has been to use molecular plasma deposition of selected metals onto polymer substrates. As described in U.S. Publication 2007/0178222, controlled conditions for ion plasma deposition can provide evenly distributed metal coatings on polymer substrates, which are both adherent and radiopaque.

Metal clad glass optical fiber waveguides have been reported in U.S. Pat. Nos. 4,407,561, 4,418,984 and 5,002,359. The metal claddings are protective jackets and are not described as microthin films strongly adhered to the underlying core of the fiber.

U.S. Pat. No. 6,282,349 describes a metal beam block surrounding a quartz surgical launch fiber to allow crimping of an extension onto the polymer jacket to hold the beam block and fiber in place. The metal block is intended to alleviate the heat generated from high power inputs required for laser pulsing.

SUMMARY OF THE INVENTION

The present invention is directed to thin metal coatings impregnated into or strongly adhered to nonmetal surfaces, particularly on polymers and composites used in small diameter wires and leads. Metal coated polymer/silica lead bodies in pacemaker leads can be produced that are resistant to flexing and are smaller than conventionally sized leads, allowing placement in desired locations in desired areas in vivo such as heart muscle. The invention also includes modification of surface properties of nanostructured thin metal coatings so that cell adhesion in vivo is promoted at the site of implant.

The coating methods described herein provide conductive, flexible metal coatings on polymer or composite thin wire or fiber leads such as those used in pacemakers. The deposited coatings are thick enough to prevent x-ray transmission, i.e., are radiopaque, yet do not affect polymer qualities such as flexibility. Flexibility is important because medical procedures may require removal or insertion of leads or wires during surgical or replacement procedures. A particular advantage of wires and leads coated in the described manner is the ability to manufacture metal coated leads having overall diameters as small as 100 nm.

Pacemaker leads manufactured in accordance with the methods and materials herein described have notable advantages over currently used metal wire conductors used by medical device manufacturers. It is well recognized that currently marketed leads experience plastic deformation fatigue due to repeated flexing after implantation. In contrast, the coated fine wires of the present invention are good conductors and retain flexibility, radiopacity, and resistance to flaking over tens of thousands of flexing cycles.

Currently, in attempts to rectify this problem of lead failure, multifilar leads consisting of two or more wire coils wound in parallel around a central axis in a spiral manner have been developed and used in some commercially available wire leads. This configuration changes the overall stress vector in the conductor body from a bending stress in a straight wire to a torsion stress in a curved cylindrical wire perpendicular to the lead axis. Plastic deformation fatigue of the metal is reduced but often not to an acceptable level. Multiple conductors need to be included to provide a backup in case of failure.

In contrast, the single solid core wire leads made in accordance with the described process do not require additional wires such as are used in multifilar coiled designs; rather, a thin, flexible single wire is small enough to be effectively implanted and used in left-heart CRT, and neurological and spinal applications where small size is critical for proper performance and minimization of side effects.

Additionally, the coated leads of the present invention are significantly less expensive to manufacture than coiled, multifilar designs. A simple manufacturing fixturing process utilizes metal ion plasma deposition in a chamber equipped to rotate a wire and allow even coatings.

The described metal coatings are extremely thin, on the order of 1-20 microns, radiopaque, and conductive as well as having high flexibility. Radiopacity allows visualization by fluoroscope or X-radiation so that placement and tracking in vivo can be enhanced for medical device components.

The process for coating fine wires is described in U.S. Application Publication No. 2007/0178222, incorporated by reference herein. A metal ion plasma deposition process is controlled such that a relatively thin but highly dense coating of macro particles is formed on a polymer substrate. When used to coat a polymer wire or lead, this provides a thin, highly adherent and radiopaque film that does not interfere with the flexibility required for manipulation of a wire inserted in the body, while at the same time allowing use of x-radiation. Because of the radiopacity, the position of an inserted wire or lead can be determined.

The present invention utilizes an ion plasma deposition (IPD) process modified to provide macroparticulate surface-layered metal films on polymer surfaces. The coatings can be deposited on flexible polymers, on other non-radiopaque materials such as ceramics, and on minimally radiopaque materials that require enhanced radiopacity. The disclosed process has an extremely high volume output and is relatively low cost compared to other vapor deposition and electroplating methods.

The modified plasma deposition process is a metal plasma deposition method where a metal is vaporized from a cathode and deposited on a substrate. It is difficult to obtain satisfactory adhesion of metals on polymers using conventional physical vapor deposition (PVD) processes, electroplating, or electro-less plating without altering the physical properties of the original substrate. For most metals deposited by typical deposition processes, adhesion is dependent on a strike layer of a metal such as titanium or chromium and even then, the polymer coating tends to delaminate if the substrate is bent, twisted or stretched. Use of the metal plasma deposition method described imbeds a coating into a polymer so that peeling and flaking are virtually eliminated.

While electroplating and electro-less plating are relatively low temperature processes (less then 70° C.), most plasma vapor deposition processes require a pre-heat cycle and glow discharge, typically requiring temperatures exceeding 200° C. Most plastics melt well below this temperature. An IPD process can be performed at a much lower temperature, allowing for low melting point plastics to be effectively coated without adversely affecting the original substrate specifications. Such low temperature deposition is achieved by controlling the deposition rate, especially the deposition of macro particles, which are produced in the described process. In general, higher macro particle deposition rates result from lower temperature depositions, while lower deposition rates result from higher temperature depositions. Macro particles are usually not charged and therefore do not induce a current on the substrate when deposited. In addition, the substrate spends less time in the plasma, so that little if any heating occurs.

The described deposition process can be used to deposit metal coatings that normally would not provide acceptable adherence or radiopacity when deposited by traditional vapor deposition methods. While tungsten, molybdenum, and iridium have a higher radiopacity at comparable thicknesses compared to more expensive metals such as gold, the thinner coatings, using shorter processing times obtained with using the described method achieve the same radiopaque results. This results in major cost savings and higher throughput, which is a significant advantage.

In addition to more economical methods and apparatus for coating manufacture, the single wires and leads coated by the described method have significantly improved thin metal coatings on the flexible materials needed for use in the small wires and leads required for manipulations in the human body.

Thin, adherent metal coatings can be produced by the described process from any metal that has an atomic number greater then 21, and a density greater then 4.5 $g/cm^2$, particularly Ti, Zr, Cr, Co, Ni, Mo, Pd, Ag, Hf, Ta, W, Ir, Pt, and Au; preferably Ag, Ti, Cu and Au. These metals can be deposited as thin films on polymer surfaces, making such highly radiopaque, thin coatings ideal for use not only on wire leads but also on catheters, valves, stents and particularly for implant devices that require flexibility.

A particular advantage of the wire leads is that digital and analog signals can be carried by the wires or leads; for example, by sending a digital signal down the silica core and/or an analog signal down the metal. Accordingly, the wires can conduct an analog or digital signal to or from a device situated remotely or, in the case of cardiac leads, from outside the body. Signal generating devices can be in communication with the wires or leads using methods well known to those skilled in the art.

DEFINITIONS

Nanoparticles and nanoparticulates refer to a range of nano and micro-sized particulates produced by cathodic-anodic plasma discharge using a cathode/anode system of creating a plasma discharge. The system is shown in FIGS. 1 and 2. The system generates so-called macros or macro particles from a metal cathode.

Macros and macro particles refer to particles larger than a single ion. Small macroparticles refer to particles from two atoms to approximately 100 nanometers (also called nanoparticles). Medium macro-particles refer to particles from 100 nanometers to about 1 micron. Large macro-particles refer to particles larger than 1 micron.

A radiopaque material does not allow passage or transmission of x-rays.

Fixturing is used in coating processes to assure film or coating homogeneity on devices that do not present flat surfaces to a deposition process. Various types of substrate motion during the coating process can be effective in maximizing the homogeneity of the film. Each point on a fixed substrate has a different spatial relationship to the source when IPD processes are used. Mobile planetary substrate fixturing typically employs constant speed mechanisms with one or more degrees of freedom designed to average the target over large substrate areas to produce more uniform coatings.

Ion beam assisted deposition (IBAD) is used to densify sputtered coatings.

As used herein, a wire lead or lead may be a nonmetal such as a ceramic or polymer or a metal, as will be apparent from the description. It is understood that the wires and leads referred to herein are not hollow tubes, but have solid cores. Unless otherwise identified, the wires or leads described herein are small diameter and single strand having a solid nonmetal core.

DETAILED DESCRIPTION

The present invention illustrates that highly adherent, thin metal coatings or films can be produced on polymer-based substrates. A controlled ion plasma deposition process produces highly adherent coatings on polymer substrates while also having higher deposition rates than other conventional plating and deposition processes used in the industry. The excellent adhesion of the coatings has made it possible to deposit radiopaque coatings directly onto polymer substrates and to produce flexible, conductive solid core single wire leads appropriate for use in cardiac pacemakers and other medical devices requiring flexible leads. Such leads are typically small in diameter and comprise polymer or ceramic cores.

The disclosed plasma deposition method is described in U.S. Publication 2007/0178222. Macro-particles greater than 1 micron in size are ejected from the cathode (target) and deposed on the substrate and actually enhance, rather than diminish, the radiopaque quality of the metal coatings. While it is generally known that cathodic arc deposition processes can achieve higher deposition rates and tend to produce more macro-particles than other types of plasma deposition processes, deliberately increasing macro-particle deposition not only enhances radiopacity of plasma deposited materials but also produces high quality thin films.

Figure 4:
FIG. 4 is a photograph showing the smooth surface texture of a plasma deposited gold film on a plastic (polyimide) substrate, at 20× magnification on a total field of 253-262 microns. Deposition conditions were controlled so that the surface was essentially free of macroparticles in the 1 micron or larger size range.
Figure 5:
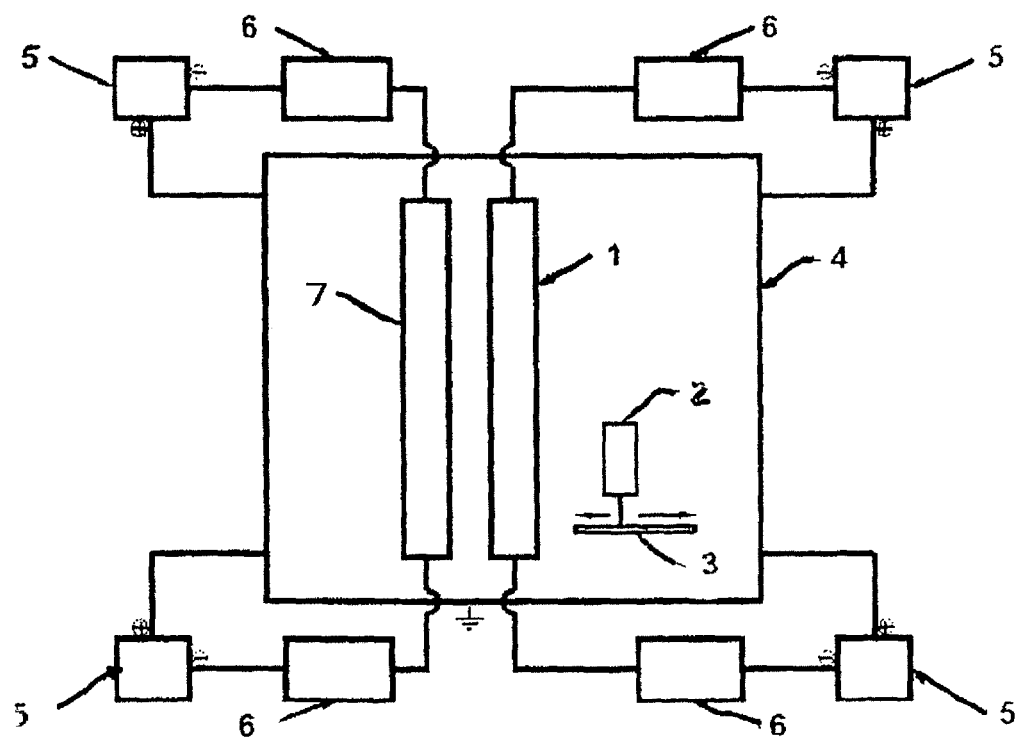
FIG. 5 illustrates an apparatus with two targets that can be used simultaneously or serially; target A (1); target B (7); substrate (2); mechanism for adjusting substrate distance from target A or target B (3); vacuum chamber (4); power supplies for control of either target (5) and optionally an arc speed control for either target (6).

Plasma deposited coatings need not be limited to a single metal such as gold. Two different targets can be used so that an initial deposition can be made with one metal that covers the substrate surface with an adherent smooth surface, such as shown in FIG. 4, followed by a different metal that can be deposited in increasing amounts of macroparticles (a continuum of particulate size in the coating) or more discontinuously by immediately adjusting the arc speed and/or substrate position relative to the target. As an example, titanium can be deposited from a first target, followed by gold deposition from a second target, in such a manner that a dense coating of gold macro particles is formed immediately over the titanium or the gold coating is deposited with a gradual increase of macroparticles.

The invention illustrates deposition of a radiopaque coating on a polymer surface using an IPD process. In one aspect the invention includes a substantially macroparticle-free coating is deposited on the substrate followed by an additional coating of macro particles, which may be from a second target material. Preferably, the coating, while not homogeneous, appears as a single layer and is deposited to a thickness of about 1 to about 100 microns. Thicker films are generally not desirable as radiopaque coatings.

The number and density of the deposited macroparticles can be determined by controlling distance of the substrate from the target and/or varying arc speed. The coating is preferably deposited continuously so that there are no discernable layers. Of course one may also deposit a first layer and a second layer so that each layer has a distinct homogeneous appearance. The macroparticles are preferably at least 1 micron in size.

The densities of deposited macroparticles may range up to 90,000/cm$^2$; and while this surface density provides excellent radiopacity properties for gold, no claim is made to an optimal density or that this density range is optimal for other metals. Nor has an optimal maximum size distribution been determined although it is believed that the ideal particle size will cluster in a range around 1 micron, which is a "medium-size" macroparticle as defined herein.

Substrates may be of any desired material but polymer based substrates are particularly preferred. Virtually any plastic substrate can be coated by the described method, including PTFE, ePTFE, polypropylene, polyester, PEEK, UHMWPE, silicone, polyimide and ABS. Polyimide, acrylates and PEEK are preferred substrates as medical devices are often constructed of these materials.

The described coatings are useful for valves, implants, catheters, stents and tubes, but are particularly advantageous for wire leads.

Suitable coatings that can be produced include gold, silver, titanium, niobium, molybdenum, zirconium and hafnium with gold being particularly preferred. Titanium may also be used, but is preferably used as an undercoat with gold macroparticles at least on the surface of the coating because gold normally provides better opacity than titanium.

Coating thickness is preferably in the micron range. This thickness typically provides good radiopacity properties, but of course can be optimized depending on the coating metal. Preferable thicknesses for gold are in the 1-20 micron range, more preferably 1, 5, 10, 15 and 20, and most preferably in the 5 micron range; for silver, preferred thickness is about 5-50 microns, more preferably 10, 20, 30 or 50 microns, and most preferably 20 microns.

The radiopaque films have unusual surfaces, comprising a dense macroparticle film surface over a substantially macroparticle-free adherent base undercoat. The coating may be homogeneous, controlled by deposition conditions, or heterogeneous, obtained by using discrete deposition conditions.

The deposition method takes advantage of the distance/current relationship with target. The closer the substrate is to an arc source, the more macro-particles will be present on the substrate. As macro particles are ejected from the target, they evaporate so that the longer the time of flight, the more material is evaporated from the particle. Additionally, either a higher current or limiting the current to a level that occurs just before an arc split tends to cause more and larger macro particles.

A motorized unit that has the ability to move a substrate closer to and farther away from the target (cathode) can be used to initially deposit a fairly macro-free film for better adhesion on a substrate positioned far away from the target, which is then followed by deposition of a more macro particle dense film with the substrate positioned close to the target, which produces a more radiopaque film or coating.

A controlled plasma deposition power source can be configured to sufficiently slow (or accelerate) the speed of the arc. The traveling speed of the arc is directly related to the amount of macro particles produced. Essentially, slowing the speed of the arc on the surface of the target (cathode) will cause it to produce more macro particles, which can be used to increase the macro particle density, thus also the film density. Conversely, increasing the speed of the arc on the cathode decreases production of macro particles, thereby providing more high energy ions that can be embedded into the surface of the substrate to produce better adhesion. U.S. Pat. No. 6,936,145 describes a mechanical switch which is one possible means to increase and decrease travel speed of the arc. Such increase and decrease of arc speed results in the deposition (without internal movement) of a fairly macro-free film for adhesion, which can be followed directly by a macro dense film by manipulating the arc speed.

Several metals due to their electronic configuration, large atomic cross section (higher atomic number in the periodic table) and density in the x-ray range may be suitable as coatings. In addition to these characteristics, the coating metal must be bio-compatible if used for coatings on medical devices. Because of these requirements, tungsten, molybdenum, tantalum, and iridium are useful for such coatings.

Typical coating rates range from 100 run to 5 microns per minute for materials such as gold or silver. It is possible to coat over 45,000 square inches per hour at a coating rate of greater than 200 run per minute. In addition to the increased coating rate and large volume, less handling per square inch is required due to the single layer coating, which translates to lower labor and higher processing rates/throughput.

The process provides embedding of thin metal coatings on nonmetal substrates, such as the polymer materials used for medical devices. Thin, conductive flexible metal coatings can be deposited by ion plasma deposition on polymers and other nonmetals such as silica and glass. Ion plasma deposition is an extremely efficient process and does not require flat surfaces in order to achieve good coating coverage so that regardless of shape, uniform coatings are readily obtained.

It has been found that the described plasma deposited metal coatings on wire leads, such as those used in pacemakers, provide features which overcome many of the disadvantages of conventionally used leads. Thin, adherent metal coatings on lead wires are conductive and when applied as a macroparticulate layer atop a particulate imbedded metal layer over a silica or silica/glass wire core provide remarkable protection from damage caused by flexing or bending. In a series of tests that conform to US Food and Drug Administration standards for bending fatigue, silver metal coated glass silica fibers underwent over 5 million bending cycles without a single failure. The results were comparable to Teflon (PTFE) coated fibers which also survived several million cycles. A notable advantage of the metal coating is the conductivity property on an extremely thin wire. Metal claddings or coax metals over wires do conduct, but are not ideal for lead wire implants because of added bulk and diameter.

In a particular example, as applied to the fabrication of pacemaker leads, a silica fiber core is coated with two layers of a metal using the described ion plasma deposition procedure. By adjusting deposition conditions, preferably by using different arc speeds, a first metal coating layer consisting of small metal particulates less than about 1 micron in size is deposited followed by slowing the arc speed so that larger particulates, i.e., macroparticles larger than 1 micron, are deposited in a second layer. If the arc speed is variably adjusted the particulate layer and the macroparticulate layer have an indefinite boundary. By stopping the deposition and restarting at a slower arc speed for depositing the second layer, the boundary between layers is defined. The actual speed used requires some optimization in order to obtain a thin adherent first coat and a dense enough second macroparticulate layer that will provide a desired radiopacity. The dual layers provide a first layer highly adherent to the substrate and the second layer provides a nanorough surface that is radiopaque yet is thin and allows flexibility of the fiber core.

The deposited metal for a lead is usually titanium or gold, but other metals can be deposited by cathodic arc plasma deposition, including platinum, silver, aluminum and tantalum as well as metal alloys. The deposition conditions will vary depending on the metal, desired thickness of the deposited layers and the relative density of the particulate and macroparticulate layers.

The thickness of the metal layers on a lead or fiber core is controlled by the deposition process and will preferably be on the order of no more than 20 microns but can be as thin as 1 micron. The diameter of a coated silica fiber or silica/glass fiber will typically be about 150-250 microns depending on the thickness of the underlying wire or fiber such as silicon or polymer.

Metal coated fibers of the present invention are optionally further coated with a top protective polymer, which will be biocompatible when used for implantable devices or leads.

Where a metal is the outer coating on a nonmetal substrate, there are several options, depending on use or desired location to implant a device or lead. Silver coatings are antibacterial and may be useful on leads placed in vivo at points susceptible to infections. Nanostructured metal surfaces will attract some types of cells so that implants or leads that feed through muscle tissue such as heart can be engineered to attract muscle cells. This may be important because foreign surfaces tend to attract fibroblasts with subsequent formation of scar tissue.

In one example of an implantable fine wire, a unipolar lead with a fiber core of glass, silica or crystalline quartz can be coated with gold or aluminum using the deposition process described herein. Conditions can be controlled to deposit the metal to about 1 to about 100 microns such that the overall width of the lead can be as low as 100 microns. Such wire leads are suitable for electrode attachment at one end.

While additional thin metal coatings can be deposited over a metal coating, such additional layers will increase the lead wire diameter although in some applications such second coating if a different metal may provide additional advantages in connection to a terminal or protection from oxidation as a lead passes through different parts of the body or is exposed externally.

Optionally, a polymer outer coating may be further added over the metal coating. The overall thickness of the wire will be determined by the method of polymer application, such as a dipping or spraying process.

Figure 6:
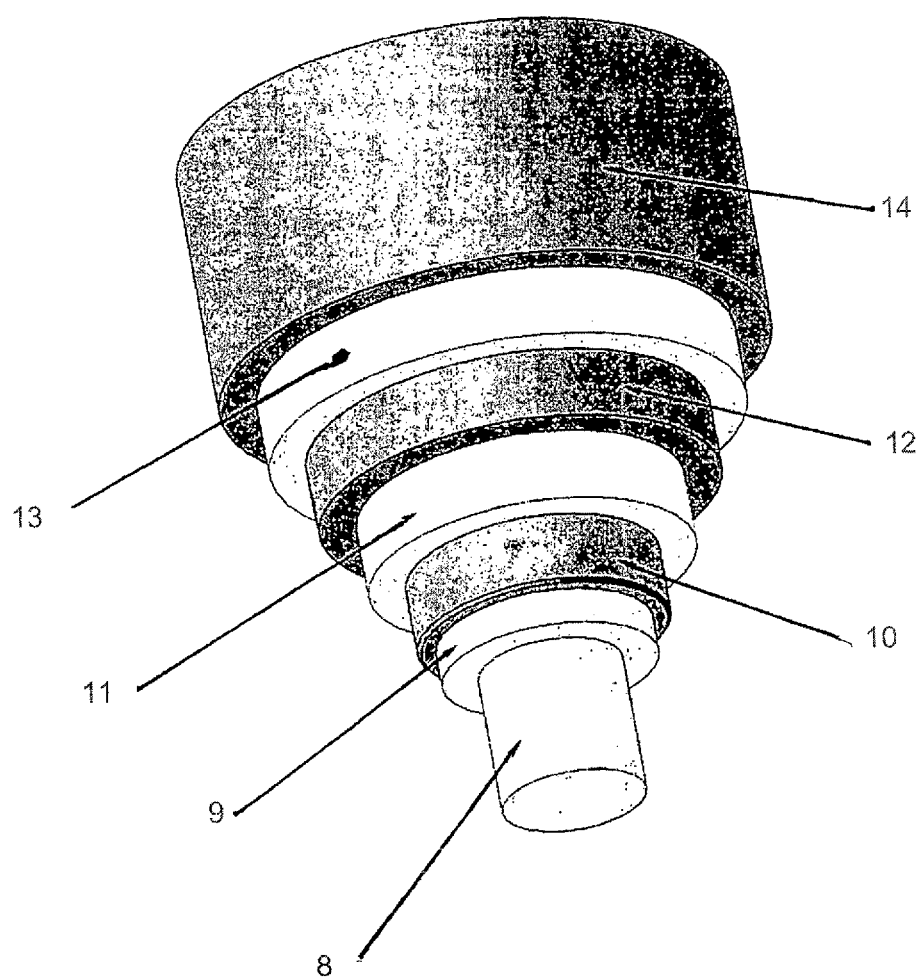
FIG. 6 is a diagram showing an example of a metal coated polyimide over a glass/silicon fiber core illustrating additional cladding with an insulator and outer jacket.

FIG. 6 is a diagram showing one embodiment of an implantable lead wire with a typical silica core fiber (1) and silica clad (2); hermetic seal (3) coated with polyimide approximately 1 um thick (4); a metal buffer coating applied using the described process (5); an insulator typically PTFE (6) placed over the metal buffer (5); a biocompatible coating, typically silicon, placed as an outer jacket (7) over the insulator (6).

Using a gold coated wire constructed of a fiber optic core (silica) with a polyimide coating to conduct both an analog and digital signal, it was shown that both signals could be successfully transmitted. Additionally, there was a silicone insulator over the gold coating that was deposited on top of the polyimide. A digital signal constructed of light pulses from a laser was used to produce a typical computer fiber optic communication. An RF signal was transmitted through the outside of the wire on the gold coating and was shown to correctly indicate an imminent break in the wire.

EXAMPLES

Example 1

Plasma Deposition Method

The modified Ionic Plasma Deposition method utilizes a controlled cathodic arc discharge on a target material to create highly energized plasma. The method differs from normal ion plasma depositions in several ways, including precise control of arc speed. This allows for faster movement, creating fewer macro particles without the use of sensors or filters, or slower movement, creating a greater amount and larger macro particles. It also gives the option of mixing the two modes to create a moderate amount of particles, or creating a near macro-free coating followed by a macro-dense coating. Alternatively, macroparticle density can also be controlled by adjusting movement of the substrate with respect to distance from the target during deposition.

Several nonmetal substrates have been coated with highly radiopaque coatings, including PTFE, ePTFE, polypropylene, polyester, PEEK, UHMWPE, silicone, polyimide, acrylates and ABS. The coatings deposited by the IPD method are highly adherent and typically have been found to imbed in polymer surfaces up to 100 nm, so that flaking and peeling are virtually eliminated.

Figure 1:
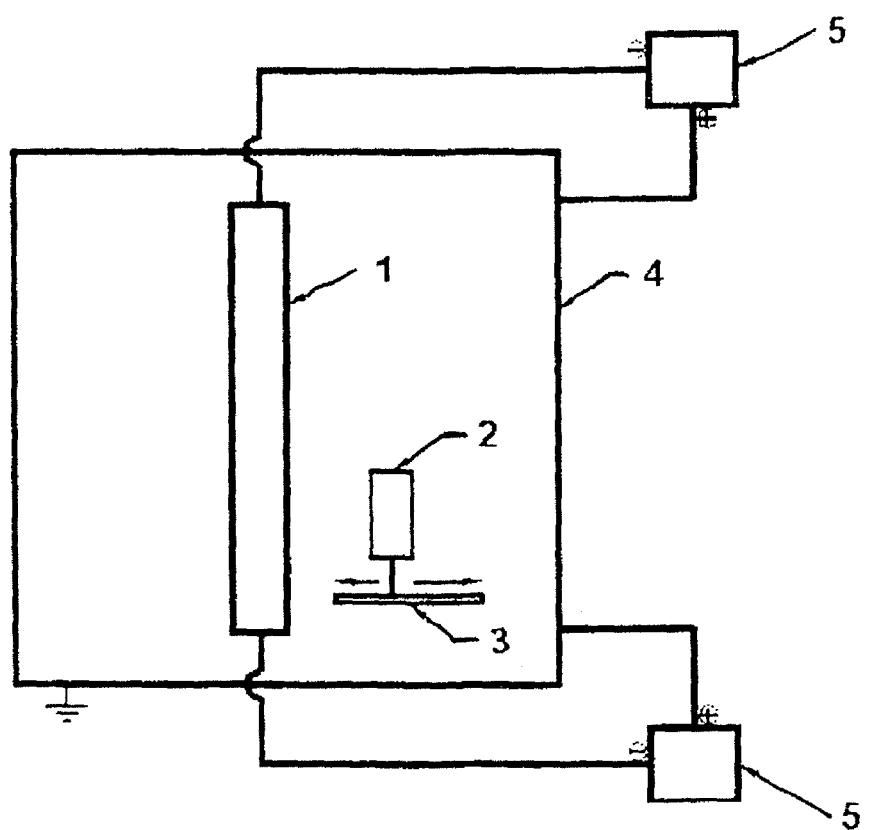
FIG. 1 is a sketch of the plasma deposition apparatus: target material (1), substrate (2), mechanism for adjusting substrate distance from the target (3), vacuum chamber (4), power supply for the target (5).
Figure 2:
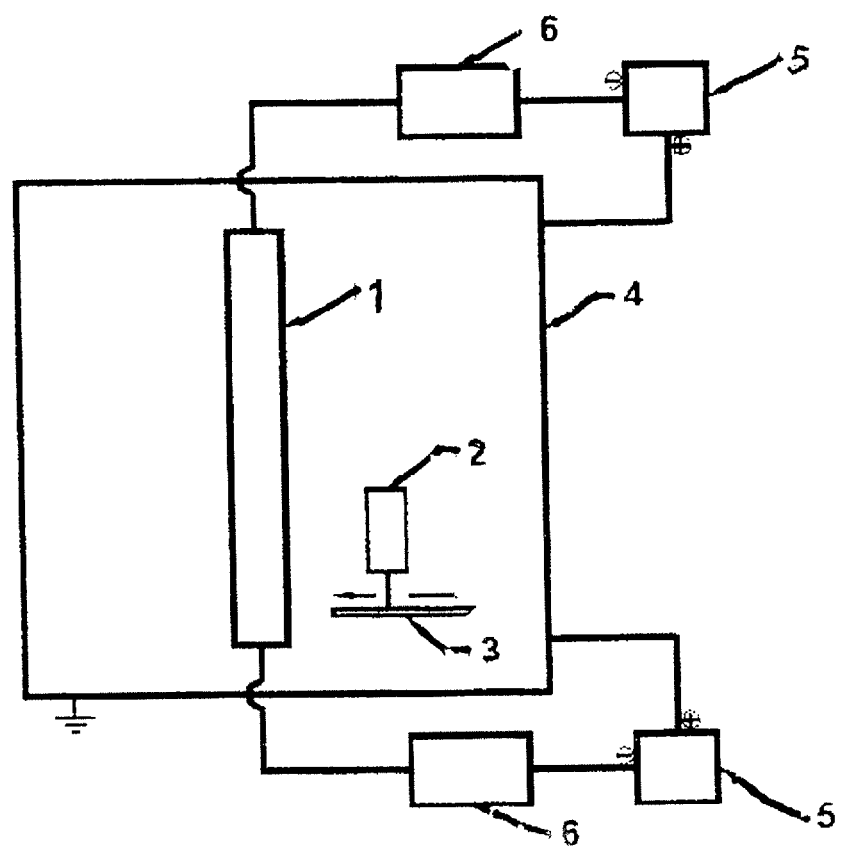
FIG. 2 is another embodiment of plasma deposition apparatus; target (1), substrate (2), mechanism for adjusting substrate distance from the target (3), vacuum chamber (4), power supply for the target (5), and arc speed control (6).

Several thin metal coatings were deposited using a modified IPD method. A typical apparatus is shown in FIG. 1 and FIG. 2 where either system provides control of the target metal deposition. Deposition conditions are adjusted to the size and type of substrate, the target material, such as gold or other biocompatible metals, and thickness of film desired. In preparing the films, a substrate, which can be as complex as a curved plastic tube, is placed at a distance from the target so that a metal/metal oxide smooth film is deposited uniformly over the surface. Thicknesses are preferably in the range of about 100 nm. FIG. 4 is a photograph at 20 fold magnification showing the surface appearance of a film deposited on a stainless steel substrate using the apparatus as shown in FIG. 1 where the substrate was relatively far from a silver target, about 24 inches. Typical operating parameters are vacuum pressure of 0.1 mT to 30 mT, operating temperatures in the range of 25° C. to 75° C.

For purposes of obtaining a highly adherent, flexible film, deposition is preferably a continuous process where the deposited film characteristics are changed by either changing arc speed (FIG. 2) or adjusting position of the substrate in relation to the target (FIG. 1) so that larger particles, i.e., macroparticles are deposited. The surface of the film on a plastic (or metal) substrate comprises a dense macroparticulate surface where the majority of the densely distributed particles are at least 1 micron in size. In order to initiate film deposition, a deposition of a metal such as gold from the target is initiated at about 24 inches from the substrate until the substrate surface is coated. The substrate is then moved to about 8 in from the target, resulting in an increasing number of macroparticles being deposited.

The coating is preferably deposited as a continuous layer; i.e., two layers with distinct physical properties. Macroparticle density throughout the film will increase from the surface of the substrate in relation to the speed with which the arc speed is changed and/or the substrate is moved in relation to the target. The final thickness of the coating can be controlled depending on the material deposited and a thickness that will provide a desired radiopacity for the intended use.

Radiopacity properties of a coating will be determined in part by its thickness and by the stopping power of the material, i.e., its ability to absorb and/or reflect x-rays. Atomic number, density and cross section all have an impact on the stopping power. Gold coatings with a thickness of 1 to 5 microns on a round substrate using the disclosed IPD method provide sufficient radiopacity for medical use.

Example 2

Thin Gold Film on Polyimide

Figure 3:
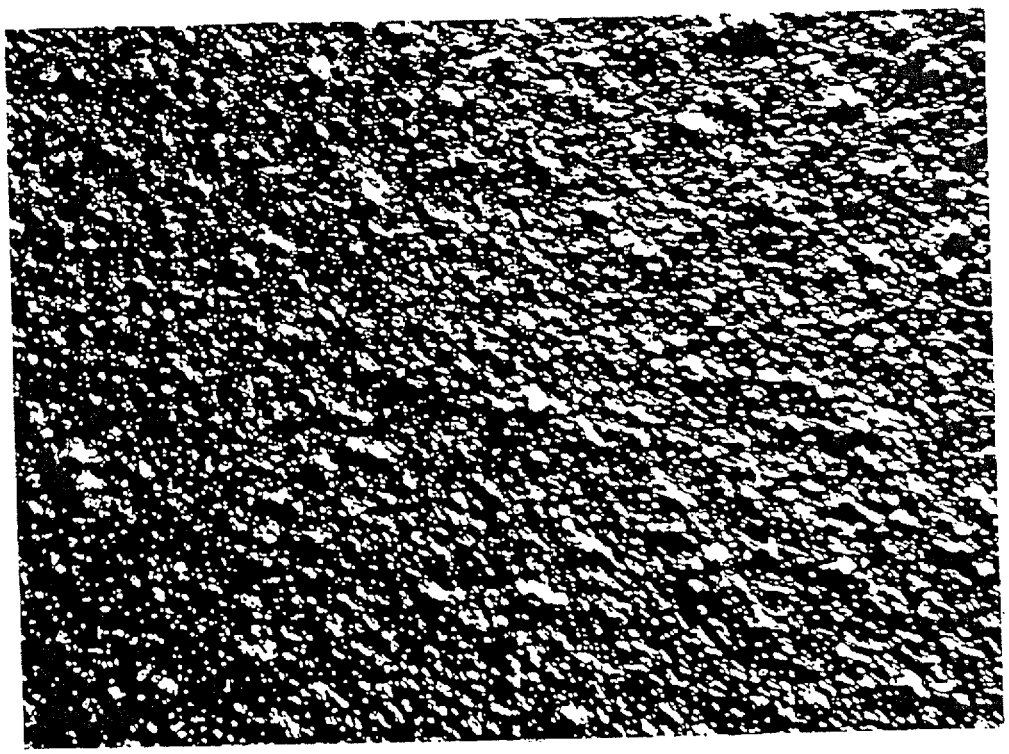
FIG. 3 is a photograph showing a plasma deposited gold film on a plastic (polyimide) substrate, at 20× magnification on a total field of 253-262 microns. Deposition conditions were adjusted to achieve a high macroparticle density. The surface was calculated to have a macroparticle density of 90,000/cm$^2$ for macroparticles that are about 1 micron or larger in size.

Samples of catheters were coated with 5, 10, 15, and 20 microns of radiopaque gold markers and tested in a conventional cath-lab system. A standard radiological procedure indicated an x-ray intensity of 60 kV and for large patients 90 kV was used. Under normal conditions (60 kV), the 10, 15, and 20 micron samples were visible. Using 90 kV, the 5 micron sample in addition to the 10, 15, and 20 micron samples were visible. The testing was performed with the prepared samples and no other biomass. The appearance of a typical gold film surface is shown in FIG. 3. The initially deposited gold has a smooth surface (FIG. 4) with few if any macroparticles.

Example 3

Thin Metal Coating on PEEK Spinal Implant

A spinal implant constructed of PEEK was coated with a 5 micron thick coating of gold using the IPD method described in example 1. The coating had an average of 100 nm macro-particles densely distributed over the coating surface. A typical macroparticle distribution of 90,000 cm$^2$ is shown in FIG. 3. The implant was masked such that when coated, only a limited area of the implant, typically not visible under x-ray irradiation, would be visible.

The coated portion of the implant was viewed with a fluoroscope at 60 kV and 90 kV with no other biomass. The fluoroscope imaged implant markings were highly visible.

Example 4

Radiopacity of Gold Coating on PEEK Spinal Implant Overlaid With Mammalian Tissue A spinal implant constructed of PEEK was coated with a 5 micron thick coating of gold deposited by the IPD method of Example 1. The coating had an average of 100 nm macroparticles densely distributed over the coating surface. The implant was masked such that when coated, only a limited area of the implant, typically not visible under x-ray irradiation, was visible. The coated part was illuminated with a fluoroscope at 60 kV and 90 kV with a one inch piece of pig flesh over the top of the implant. The resulting fluoroscope images showed that the implant markings were clearly visible, providing evidence that similarly coated implants will be visible through tissue.

Example 5

Flexible Metal Clad Fiber Wire

Polyimide Coated Glass Silica Fiber Coated With Silver

This example provides a polymer encased wire coated with a metal which is resistant to plastic deformation fatigue, conductive and radiopaque.

A high-bond-strength micron-thick (approximately) silver metal conductive surface was applied to a polyimide glass silica fiber core wire using ion plasma deposition to deposit the silver on the surface of the polyimide, see FIG. 6.

Several different samples of single polyimide coated glass fibers approximately 250 microns in diameter were plasma coated with 0.5 and 5 microns of radiopaque silver markers and tested in a conventional cath-lab system. A standard radiological procedure indicated an x-ray intensity of 60 kV and 90 kV. Under normal conditions (60 kV), the fibers thinly coated with 5 microns of plasma deposited silver/silver oxide were visible. Using 90 kV, the 5 micron sample was visible.

Conductivity of a one meter piece of the silver coated polyimide encasing the glass silicone core fiber was tested. Prior to fatigue testing, the conductivity was approximately 25 ohms. The testing was performed with the prepared samples and no other biomass.

The strength of the coated fiber was also tested. Due to the combination of the glass, polymer and metal, the fiber body construction was not expected to be subject to "plastic fatigue." However, unexpectedly, neither the silica core/polymer, nor the thin conductive layer experienced plastic fatigue. Enhanced durability as shown by the lack of fatigue was demonstrated in independent durability testing, see Table 1.

TABLE 1

| Item | Description | Received | Test Radius (mm) | EMT Sample # | # of Cycles |
| --- | --- | --- | --- | --- | --- |
| 2 | Fiber, Uncoated | Jan. 18, 2009 | 1.5 | 2D | 1,979,698 |
| 3 | Fiber, Uncoated | Jan. 5, 2009 | 3 | 3A | 1,844,171 |
| 4 | Fiber, Uncoated | Jan. 5, 2009 | 3 | 4A | 5,003,183 |
| 5 | Fiber, Silver Coated | Jan. 5, 2009 | 1.5 | 1B | 2,119,073 |
| 6 | Fiber, Silver Coated | Jan. 5, 2009 | 1.5 | 2B | 1,865,026 |
| 7 | Fiber, Silver Coated | Jan. 5, 2009 | 3 | 3B | 5,156,569 |
| 8 | Fiber, Silver Coated | Jan. 5, 2009 | 3 | 4B | 2.619,679 |
| 9 | Fiber, PTFE Coated | Jan. 5, 2009 | 3 | 1C | 5,156,601 |
| 10 | Fiber, PTFE Coated | Jan. 5, 2009 | 3 | 2C | 2,518,646 |

The survivability of the metal coated polymer/silica fiber was tested for fatigue by bending the fiber over a mandrel of a specific radius a set number of times. To mimic use in medical implants, the fiber was tested as if it were being used as a lead for a pacemaker in the body. This testing is very rigorous and must conform to specific US Food and Drug Administration regulations. For current FDA approval, it is required that leads be subjected to a 6 mm mandrel at least 40,000 times. As can be seen in Table 1, the silver coated fiber successfully completed almost two million cycles over a 1.5 mm mandrel and over five million cycles over a 3 mm mandrel. No fiber failed during the testing. No changes in conductivity and radiopacity were found after fatigue testing.

An independent acute single animal in vivo test was performed on a fiber system to ensure the viability of the technology and the ability of the fiber to deliver the proper amount of current and voltage to an appropriate place in the heart. This testing was performed in a single acute dog model. As shown in Table 2, the fiber lead preformed exactly the same as an off-the-shelf commercial lead.

TABLE 2

|  | Pulse Width (ms) | Capture Voltage/Pacing Threshold (V) | Impedance at Capture (Ω) |
| --- | --- | --- | --- |
| Control Lead (Medtronic) | 1 | 0.5 | 650 |
|  | 0.5 | 0.5 | 650 |
|  | 0.25 | 0.5 | 667 |
|  | 0.13 | 0.8 | 650 |
|  | 0.07 | 1.1 | 667 |
| Prototype Fiber Lead | 1 | 0.5 | 617 |
|  | 0.5 | 0.5 | 617 |
|  | 0.25 | 0.5 | 650 |
|  | 0.13 | 1.1 | 633 |
|  | 0.07 | 1.6 | 633 |

To further increase the durability, the metal conductor can be encased in an insulating polymer jacket. This system is not limited to silver coated polyimide. Other conductive, ductile metals such as titanium, aluminum, gold, platinum, tantalum, or others, as well as metal alloys can be used.

Example 6

Transmission of Analog or Digital Signals

The described metal coated thin flexible wires can be used with medical devices for implants or in various applications requiring communication or control by using analog or digital signal transmission.

In this example, a gold coated wire, constructed of a fiber optic core (silica) with a polyimide coating was used to conduct both an analog and digital signal. A silicone insulator over the gold coating was deposited on top of the polyimide. A digital signal constructed of light pulses from a laser was used in a typical computer fiber optic communication. An RF signal was transmitted through the outside of the wire on the gold coating.

While the digital internal signal was used for communication, the RF analog signal acted as an early warning of immanent wire breakage, providing sensing of a possible break in the wire BEFORE the wire actually breaks. The RF analog signal enables detection of a break in part of the gold coating (and/or in the silicone overcoat) that will eventually lead to a break in the polyimide and silica core.

To test the warning system, test breaks were made in the gold coating. A break was detected by the RF analog signal 100% of the time before the digital signal was affected. This provides a safety feature for leads used in cardiac implants and in applications such as aeronautical sensors in drones, planetary rovers and many other applications where wire or lead failures may have significant serious or deadly consequences.

I claim:

1. A thin single flexible wire or lead comprising a polyimide coated fiber optic silica core on which is deposited an ion plasma 1-20 micron thick single or dual layer radiopaque metal coating wherein the wire operably connects to an external or internal device to transmit an RF signal through the metal coating and a digital communication signal through the silica core.

2. The wire or lead of claim 1, which has a flexibility up to at least about five million cycles, said flexibility being retained during and after in vivo implantation.

3. The wire or lead of claim 1 wherein the single layer coating comprises heterogeneous sized nanoparticulates ranging from about 2 atoms at the wire or lead surface up to about 1 micron at the coating surface.

4. The wire or lead of claim 1 which has a diameter of about 100 to about 250 microns.

5. The wire or lead of claim 1 wherein the deposited metal is aluminum, copper, palladium, titanium, platinum gold, silver, or combinations thereof.

6. The wire or lead of claim 1 wherein the ion plasma deposited metal coating density is about 1000 to about 90,000 macroparticles/cm$^2$.

7. The wire or lead of claim 1 wherein the metal coating is silver/silver oxide.

8. The wire or lead of claim 7 wherein the silver/silver oxide coating is adhered to a helical or mesh scaffold encasing the silica core.

9. The wire or lead of claim 1 wherein the dual layer comprises a first deposited adherent layer of metal macroparticulates having a range of sizes from about two atoms up to about 1 micron and a dense, second deposited layer of metal macroparticles having a size about 1 micron.

10. The wire or lead of claim 1 which is in operable communication with an external or internal medical device.

11. The wire or lead of claim 10 wherein the medical device is a cardiac pacemaker.

12. The wire or lead of claim 1 wherein the external device is comprised within a system subject to vibration.

13. The wire or lead of claim 1 wherein the wire comprises a polyimide coated fiber optic silica core coated with gold or titanium over which is deposited a silicone insulator.

14. The wire or lead of claim 13 wherein the deposited gold or titanium transmits both an analog and a digital signal through the gold or titanium coating and the silica core from an external medical device to monitor the fiber optic communication and the integrity of the wire in communication with the medical device.

15. The wire or lead of claim 13 which is connected to a medical implant.

16. The wire of claim 1 wherein the RF signal monitors integrity of an implanted wire or lead.

17. The wire of claim 1 wherein the digital communication signal is constructed of laser light pulses.

* * * * *